United States Patent [19]

Jacquet et al.

[11] 4,363,797
[45] Dec. 14, 1982

[54] POLYASPARTIC ACID DERIVATIVES, THEIR PREPARATION AND THEIR USE IN COSMETIC COMPOSITION

[75] Inventors: Bernard Jacquet, Antony; Christos Papantoniou, Montmorency; Gérard Land, Epinay; Serge Forestier, Claye Souilly, all of France

[73] Assignee: Societe Anonyme dite: l'Oreal, Paris, France

[21] Appl. No.: 100,882

[22] Filed: Dec. 6, 1979

Related U.S. Application Data

[63] Continuation-in-part of Ser. No. 5,941,573, Sep. 12, 1978, abandoned.

[30] Foreign Application Priority Data

Sep. 14, 1977 [FR] France .............................. 77 27770

[51] Int. Cl.$^3$ ............................................... D06P 3/04
[52] U.S. Cl. ........................................ 424/70; 8/406; 8/408; 132/7; 424/71; 424/72; 528/322
[58] Field of Search ........................... 424/70; 528/322

[56] References Cited

U.S. PATENT DOCUMENTS 3,846,380 11/1974 Fujimoto et al. ...................... 424/70

FOREIGN PATENT DOCUMENTS 1344212 10/1963 France .................................. 424/70
44-22440 9/1969 Japan ................................... 424/70
49-32065 8/1974 Japan ................................... 424/70

*Primary Examiner*—Dale R. Ore
*Attorney, Agent, or Firm*—Cushman, Darby & Cushman

[57] ABSTRACT

Novel polymers useful, in particular, in cosmetic compositions for application to the hair are described. These random polymers can be represented by the general formula:

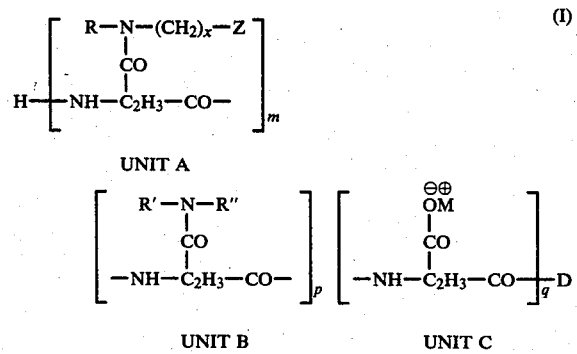

in which:

Z represents a mercapto radical or a sulphonic acid radical, which is free or is in the form of an alkali metal or an alkaline earth metal salt, x is an integer from 2 to 6, R represents a hydrogen atom or a lower alkyl radical, each R' independently represents a hydrogen atom, a lower hydroxyalkyl group, an alkyl group having 1 to 18 carbon atoms or an alkenyl group having at most 18 carbon atoms, each R" independently represents a hydrogen atom, a lower hydroxyalkyl group or a lower alkyl group, or R' and R", together with the nitrogen atom to which they are attached, form a 6-membered ring, which can contain, apart from the said nitrogen atom, an oxygen or nitrogen atom, M represents a hydrogen atom, an alkali metal atom or half an atom of an alkaline earth metal, D represents a

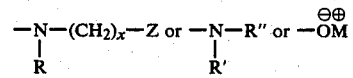

group, R, x, Z, R', R" and M being as defined above, m is a positive integer corresponding to the number of units A in the polymer, p and q are each independently 0 or a positive integer corresponding to the number of units B and C, respectively, in the polymer, such that the sum m+p+q is from about 15 to about 500.

8 Claims, No Drawings

POLYASPARTIC ACID DERIVATIVES, THEIR PREPARATION AND THEIR USE IN COSMETIC COMPOSITION

This application is a continuation-in-part of Ser. No. 941,573, now abandoned.

The present invention relates to derivatives of polyaspartic acid, their preparation and their use in cosmetic compositions.

In particular, this invention provides polymers derived from polyaspartic acid, which correspond to the general formula:

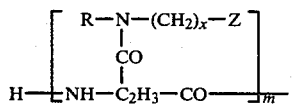

UNITS A

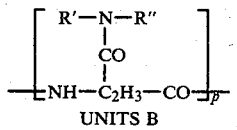

UNITS B

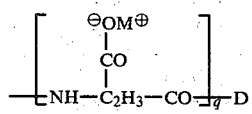

UNITS C in which Z represents a mercapto radical or a sulphonic acid radical, said radical being free or in the form of an alkali metal or an alkaline earth metal salt, x represents an integer from 2 to 6, R represents a hydrogen atom or a lower alkyl radical, each R' independently represents a hydrogen atom, a lower hydroxyalkyl group, an alkyl group having 1 to 18 carbon atoms or an alkenyl group having at most 18 carbon atoms, and each R" independently represents a hydrogen atom, a lower hydroxyalkyl group or a lower alkyl group, or R' and R" together with the nitrogen atom to which they are attached form a 6-membered ring, which can contain another heteroatom which is oxygen or nitrogen, M represents a hydrogen atom, an atom of an alkali metal or half an atom of an alkaline earth metal, D represents

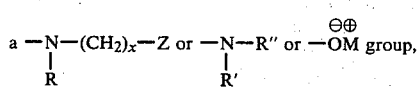

R, x, Z, R', R" and M being as defined above, m is a positive integer corresponding to the number of units A in the polymer, and p and q are independently 0 or a positive integer corresponding to the number of units B and C, respectively, in the polymer, such that the sum m+p+q is from 15 to 500.

In the units A, B or C of the formula (I), the —$C_2H_3$— group can represent either the

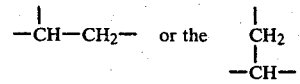

group, i.e. the nitrogen atom can be attached to the carbon atom to which the chain group carbonyl or to which the side-chain carbonyl group is attached.

Thus, for example, the units A are either:

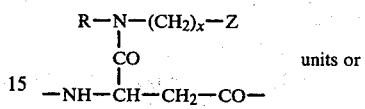

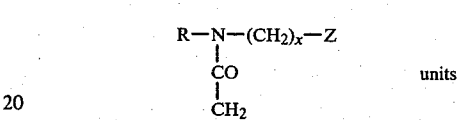

or mixtures of these.

Among the polymers of formula I, are those polymers for which $$\frac{m}{p+q}$$

is equal to or greater than 0.1.

It should be understood that although the general formula might imply that the polymer, when units B and/or C are present, is a block co-polymer, it will normally be a random copolymer.

It should be noted that in a given polymer of the formula (I), the units B can either be all identical, or different, depending on whether all the R' radicals and all the R" radicals are the same or different, respectively.

In general the values of individual radicals R' and R" are such that there are up to 10 different units B in the polymer, preferably 1 to 3 different units B.

In formula (I), when the substituent Z is a salified mercapto or sulphonic acid group, the salt is preferably a salt of sodium, potassium, magnesium, calcium, strontium or barium; if R represents a lower alkyl, it is preferably an alkyl having 1 to 4 carbon atoms, for example methyl, ethyl, n-propyl, i-propyl or n-butyl; if R' or R" represent a hydroxyalkyl group, it is preferably a hydroxyalkyl having 2 to 4 carbon atoms, for example a β-hydroxyethyl, γ-hydroxypropyl or 1-hydroxypropan-2-yl group; if R' represents an alkyl group containing from 1 to 18 carbon atoms, it is in particular a methyl, ethyl, propyl, butyl, hexyl, octyl, decyl, dodecyl, tetradecyl, hexadecyl or octadecyl radical; if R' represents an alkenyl group containing from 2 to 18 carbon atoms, it is especially an oleyl radical; if R" represents a lower alkyl group, it is preferably an alkyl group having from 1 to 4 carbon atoms; if R' and R" together with the nitrogen atom to which they are attached represent a 6-membered ring, the said substituents R' and R" together preferably represent a pentamethylene, 3-oxa-pentamethylene or N-methyl-3-azapentamethylene group.

In formula (I), the various units can have the L or D configuration or can be present in the form of mixtures of stereoisomers.

The invention also provides a process for the preparation of the polymers of formula (I). This process is characterized in that polydehydroaspartic acid of the formula:

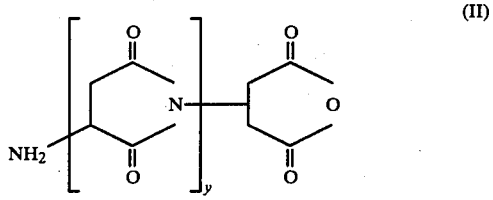 (II)

in which y is an integer from 15 to 500, is reacted with an amine of the formula:

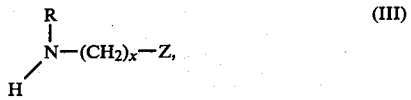 (III)

$m_1$ mols of amine being reacted per mol of polydehydroaspartic acid, $m_1$ being an integral or non-integral number which is from 1 to $y+1$, (or greater than $y+1$ if an excess of amine of the formula (III) is used), after which, if $m_1$ is less than y, the product obtained is either reacted with one or more amines of the formula:

 (IV)

and/or hydrolysed with an alkali metal base or an alkaline earth metal base. Of course it is possible to react the polymer first with the amine of formula (IV) and then with the amine of formula (III) provided that the amount of amine of formula (IV) is less than $m_1$ moles per mole of polymer.

The products of formula (I) in which Z represents a sulphonic acid group can be obtained either directly by reaction of the amine of the formula (IIIa);

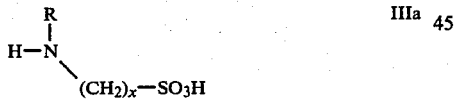 IIIa salified with an alkali metal base or an alkaline earth metal base, or by reaction of an amine of the formula IIIb

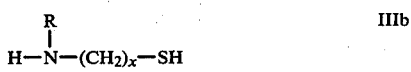 IIIb which may or may not be salified, followed by reaction of the product obtained with a suitable oxidising agent such as hydrogen peroxide in the presence of an organic acid.

Polydehydroaspartic acid can be obtained in accordance with the techniques described in the literature. Thus Fox and Coll (Analytical method of Protein Chemistry, Vol IV p. 127; edited by P. Alexander and H. P. Lundgreen, Pergamon Press) prepare polydehydroaspartic acid by heating aspartic acid, optionally in the presence of phosphoric acid. KOVACS et al., J. Org. Chem. 26, 1,081 (1961) obtain polydehydroaspartic acid by prolonged heating (100 hours) of aspartic acid in tetralin or in vacuo. French Pat. No. 70/24,831, describes the preparation of polydehydroaspartic acid by heating aspartic acid in the presence of phosphoric acid in vacuo at 170°–200° C., whilst ensuring that the surface of the reaction mixture is constantly renewed.

These various techniques of preparation of polydehydroaspartic acid exhibit numerous disadvantages:

The polymerisation in tetralin is very slow and leads to heavily coloured polymers being obtained, as a result of the product being maintained at a high temperature.

The use of liquid or very viscous acid catalysts (phosphoric acid or polyphosphoric acid) does not allow the reaction to be carried out in an apparatus of the conventional type and requires a delicate separation of the catalyst from the polymer, as well as requiring the use of large volumes of solvents.

It has now been found that if the polymerisation is carried out in the presence of a solvent of high boiling point such as diphenyl ether and a solid acid catalyst in the form of an ion exchange resin, at a temperature of 200°–230° C., under normal pressure, a polymer consisting of polydehydroaspartic acid, which is only very slightly coloured and possesses desirable properties, can be obtained within a short time (say 2–4 hours) and with virtually quantitative yields. The ion exchange resin must be sufficiently acid to be able to act efficiently as a catalyst. Hence, strongly acid ion exchange resins should be used, such as Amberlite IR 120 H. The term "solvent of high boiling point" as used herein means a solvent which boils at a temperature of at least 200° C.

This process, which also forms part of this invention, exhibits numerous advantages over the techniques described in the literature, namely:

The replacement of tetralin by diphenyl ether surprisingly leads to a very marked speeding-up of the course of the reaction. This results in a great reduction in the heating time and hence in slight colouration of the polymer obtained.

The use of a solid acid catalyst makes it possible to carry out the polymerisation in conventional apparatus and makes it very easy to isolate the polymer by simply filtering off the mixture of polymer and resin, and dissolving the polymer in a small amount of a suitable solvent such as dimethylformamide or N-methylpyrrolidone.

The solution can be used in the form in which it is obtained or the polymer can be isolated by precipitation by means of a non-solvent, for example in order to characterise the polymer. This operation does not require copious washing of the polymer to remove the acid catalyst, as is the case with the method described in French Pat. No. 70/24831.

Another advantage of this process resides in the possibility of recycling the solvent and the acid catalyst. Experience has shown that the solvent and the catalyst can be re-used 5 times, for example, without intermediate purification. The polydehydroaspartic acid can be obtained in each case with equivalent yields and equivalent physico-chemical properties.

Various samples of polydehydroaspartic acid used as the starting materials for the preparation of the derivatives of the present invention have been prepared by employing one of the following methods. It should be noted that the viscosity measurements made enable one to determine that the polymer contains 15 to 500 recurring units.

and HARRY'S COSMETICOLOGY, Lenoard Hill Books, 1973.

The following Examples further illustrate the present invention.

EXAMPLE 1

Polymer of the formula I, with $p=q=0$, $x=2$, $R=H$, $Z=$mercapto.

19.4 g of polydehydroaspartic acid obtained according to method A are dissolved in 100 cm$^3$ of dimethylformamide. The solution is deoxygenated by bubbling nitrogen through it, and 15.4 g of cysteamine in 50 cm$^3$ previously degassed dimethylformamide are added. The mixture is kept under a nitrogen atmosphere for 3 hours and 200 cm$^3$ of alcohol are then added. This mixture is filtered and the precipitate is dried under reduced pressure. 28 g of a polymer which is water-soluble under alkaline conditions are thus obtained.

Analysis: Calculated %: C 41.37, H 5.74, N 16.09. Found %: C 41.20, H 5.61, N 15.90.

EXAMPLE 2

Polymer of the formula I, with $p=q=0$, $x=2$, $R=H$, $Z=$sulphonic acid.

17.4 g of the polymer obtained in Example 1 are suspended in 50 cm$^3$ of acetic acid. 30 cm$^3$ of 30% strength hydrogen peroxide are added and the reagents are left in contact at ambient temperature for 4 days. The acetic acid is distilled under reduced pressure at 40° C. and the polymer obtained is dried. 19 g of a hygroscopic white powder are thus obtained.

EXAMPLE 3

Polymer of the formula I, with $p=q=0$, $x=2$, $R=H$, $Z=-SO_3Na$.

29.1 g of polydehydroaspartic acid obtained according to method A are dissolved in 150 cm$^3$ of dimethylformamide. 43.1 g of the sodium salt of taurine are added and the mixture is heated to 150° C. for 15 hours. The suspension is cooled and the polymer is filtered off. After washing with alcohol and drying under reduced pressure, 68 g of an easily water-soluble slightly coloured powder are obtained.

EXAMPLE 4

Polymer of the formula I, with $q=0$, $x=2$, $Z=SO_3Na$, $R'=$dodecyl, $R=R''=H$ and $p/m=0.11$.

29.1 g of polydehydroaspartic acid obtained according to Method A are dissolved in 150 cm$^3$ of dimethylformamide. 5.5 g of n-dodecylamine are added and the reaction mixture is heated for 24 hours at 80° C. 39.75 g of the sodium salt of taurine are then added and the mixture is heated for 8 hours at 150° C. After filtering, and washing with alcohol, 63.5 g of water-soluble polymer are obtained.

Following the same method of working, the polymers shown below, of the general formula I (with $R=H$ and $q=0$) were prepared:

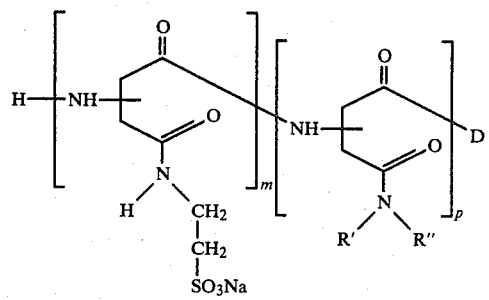

| Example | R' | R" | m/p | Yield |
|---|---|---|---|---|
| 5 | H | C$_4$H$_9$ | 4 | 96 |
| 6 | H | C$_{18}$H$_{37}$ | 9 | 81 |
| 7 | —C$_2$H$_4$—O—C$_2$H$_4$— | | 1 | 83 |
| 8 | H | CH$_2$CH$_2$OH | 0.11 | 50 |
| 9 | H | " | 0.25 | 64 |
| 10 | H | " | 0.43 | 60 |
| 11 | H | " | 0.67 | 55 |
| 12 | H | " | 1 | 64 |

EXAMPLE 13

Polymer of the formula I, with $p=q=0$, $x=2$, $R=CH_3$ and $Z=-SO_3Na$.

9.7 g of polydehydroaspartic acid obtained according to method A are dissolved in 50 cm$^3$ of dimethylformamide. The mixture is heated to 110° C. and 16.1 g of the sodium salt of N-methyltaurine are then added at this temperature. The reaction mixture becomes homogeneous. It is stirred for 30 minutes at 110° C. and then allowed to cool. The polymer which has precipitated is filtered off, washed with methanol and dried under reduced pressure. 22 g of a water-soluble beige product are obtained.

EXAMPLE 14

Polymer of formula I, with $m:p:q=8:1:1$, $x=2$, $Z=SO_3Na$, $R'=$dodecyl, $R=R''=H$, $M=Na$.

29.1 g of polydehydroaspartic acid obtained according to method A are dissolved in 150 cm$^3$ of dimethylformamide. Dodecylamine (5.5 g) is added and the mixture is heated for 24 hours at 80° C. Then 35.28 g of the sodium salt of taurine are added and the reaction mixture is heated for 8 hours at 150° C. After filtering and washing with ethanol, the precipitate is collected and dissolved in 150 cm$^3$ of water containing 1.2 g of sodium hydroxide. After agitating for 4 hours at room temperature, the water is evaporated under reduced pressure and 65 g of an easily water-soluble polymer are obtained (colour=pale yellow).

EXAMPLE 15

Polymer of the formula I, with $m/q=1$, $p=0$, $x=2$, $Z=SO_3Na$, $R=H$ and $M=Na$.

29.1 gm of polydehydroaspartic acid obtained according to method A are dissolved in 150 cm$^3$ of dimethylformamide. 22 gm of the sodium salt of taurine are added, the reaction mixture is heated for 15 hours at 150° C., and then allowed to cool. After filtering, washing with ethanol and drying, 48 gm of a product are obtained which are dissolved in 150 cm$^3$ of water containing 6 gm of sodium hydroxide. After agitating for 4 hours at room temperature, water is evaporated under

METHOD A

A mixture of 150 g of L-aspartic acid and 75 cm³ of 85% strength ortho-phosphoric acid is heated for 3 to 4 hours at 180° C. under reduced pressure in a 3 liter flask fitted with a rotary evaporator. At the end of the reaction, the mixture is allowed to cool and the viscous syrup obtained is then dissolved in 1 liter of dimethylformamide. 1 liter of water is added slowly to the solution thus obtained. The precipitate is filtered off, washed with water to remove the phosphoric acid and dried in an oven under reduced pressure at 150° C. for 24 hours. 104 g of polydehydroaspartic acid are thus obtained in the form of a white product which has a reduced viscosity of 25 ml/g (as a 0.5% solution (c) in dimethylformamide at 25° C. (t).

METHOD B

Using a method analogous to method A, but working at 140° C. instead of 180° C., 95 g of polydehydroaspartic acid are obtained, having a reduced viscosity of 8 ml/g (t=25° C.; c=0.5% in dimethylformamide).

METHOD C

A suspension of 97 g of acid resin (containing about 50% of water), marketed under the name Resin IR120H, in 150 cm³ of tetralin, is heated under reflux in a 1 liter flask equipped with a Dean and Stark attachment. After having distilled the water, 50 g of L-aspartic acid are added and the mixture is heated under a nitrogen atmosphere for 30 hours, whilst distilling the water-tetralin azeotrope. The mixture is then allowed to cool and is filtered. The precipitate, a mixture of resin and polydehydroaspartic acid, is washed with hexane. After addition of 400 cm³ of dimethylformamide, the mixture is filtered and the polydehydroaspartic acid is then precipitated from the filtrate by adding water. The precipitate is filtered off and dried for 24 hours at 150° C. under reduced pressure. 31 g of polydehydroaspartic acid are thus obtained in the form of a light brown product having a reduced viscosity of 4 ml/g (t=25° C., c=0.5% in dimethylformamide).

METHOD D

A suspension of 50 g of L-aspartic acid and 50 g of previously dried Resin IR 120H in 150 cm³ of diphenyl ether is gradually heated to 230°–240° C. in a 500 cm³ flask equipped with a Dean and Stark attachment. The water formed during the polycondensation reaction begins to distil from 200° C. onwards. The mixture is heated at between 230° and 240° C. for 2 to 3 hours and is then allowed to cool and is filtered. The precipitate containing the resin and the polydehydroaspartic acid is washed with benzene. After adding 200 cm³ of dimethylformamide, the mixture is filtered and the polydehydroaspartic acid is precipitated from the filtrate by means of 500 cm³ of ethanol. This precipitate is filtered off, washed with ethanol and then with isopropyl ether, and dried under reduced pressure for 24 hours at 150° C. 33 g of polydehydroaspartic acid are obtained in the form of a light beige product having a reduced viscosity of 10 ml/g (t=25° C., c=0.5% in dimethylformamide).

Using varying proportions of aspartic acid and of Resin IR 120H, the following polymers were prepared under the same conditions:

| Method | dR/Aa** | Heating time | Yield | Reduced viscosity* |
|---|---|---|---|---|
| E | 0.1 | 8 hours | 99% | 12 ml/g |
| F | 0.5 | 3 hours | 76% | |
| G | 0.25 | 2 hours 30 mins | 99% | |

*(t = 25° C.; c = 0.5%, dimethylformamide)
**Ratio of the weight of dry resin to the weight of aspartic acid.

These last methods (methods D, E, F and G) illustrate the process of the present invention for the preparation of polydehydroaspartic acid.

The polymers of the formula I have valuable properties which make it possible to use them as adjuvants in cosmetic compositions and in particular in cosmetic compositions for the hair.

In particular, they can be used in shampoos, in wavesetting lotions, in rinsing lotions to be applied before or after a shampoo, between the two stages of a shampoo, before or after dyeing or bleaching, or after permanent waving, in wavesetting lotions, in shaping lotions (also referred to as brushing lotions), in restructuring lotions, in hair treatment lotions to be applied before or after dyeing or bleaching, before or after a shampoo or before or after permanent waving, or in dyeing compositions. In such compositions, they have the property of improving the hold of the hair, to which they impart, in particular, bulk and springiness.

The present invention accordingly provides cosmetic compositions, especially cosmetic compositions for hair and for the skin, which contain, as an adjuvant, at least one polymer of the formula I as defined above.

Preferably, the compositions according to the invention contain the polymer of the formula I in an amount from 0.1 to 10% by weight and especially from 0.1 to 5% by weight.

The compositions of the invention are, for example:

(a) shampoos which principally contain from 3 to 50%, preferably from 3 to 20%, by weight of anionic, non-ionic, amphoteric, cationic or zwitter-ionic detergent in an aqueous excipient;

(b) wavesetting lotions which principally contain from 0.1 to 5% by weight of a cosmetic resin in an aqueous or aqueous-alcoholic excipient;

(c) rinsing lotions (referred to as "rinses"), non-rinsed waveset strengthening lotions, restructuring lotions or shaping lotions ("brushing" lotions). In addition to the polymer of the formula I, these lotions also contain, for example, conditioning agents and film-forming polymers in aqueous or aqueous-alcoholic solution;

(d) dyeing compositions and dyeing carriers, especially oxidation dyeing compositions. These compositions in general contain, in addition to the polymer of the formula I and the oxidation dyestuffs and/or direct dyestuffs, various ingredients which allow the product to be presented in the form of a cream (for example soaps, fatty alcohols, emulsifiers and fatty amides), and an alkaline agent. Where these dyeing compositions contain quaternary derivatives, a pH of about 8.5 is preferable; the alkaline agent can, for example, be added at the time of use; and (e) products for use in the bath.

The cosmetic compositions of the present invention in order respects possess the usual properties of such compositions, as described in works on cosmetology, for example HANDBOOK OF COSMETIC SCIENCE by H. W. Hibbott (PERGAMON PRESS 1963)

reduced pressure. The residue is washed with ethanol and dried. 53 gm of an easily water-soluble polymer are obtained.

EXAMPLES OF COSMETIC COMPOSITIONS

Example I

An anionic shampoo is prepared by mixing the following:

| | |
|---|---|
| Sodium $C_{12}$–$C_{14}$—alkyl-ether-sulphate, the ether containing 2.2 mols of ethylene oxide | 12 g |
| Hydroxypropylmethylcellulose | 0.4 g |
| Polymer of Example 3 | 3 g |
| Triethanolamine q.s.p. | pH 6 |
| Water q.s.p. | 100 g |

This shampoo facilitates the combing-out of wetted hair and causes the head of hair to exhibit a good hold after drying.

Example II

An anionic shampoo is prepared by mixing the following:

| | |
|---|---|
| Sodium $C_{12}$–$C_{14}$—alkyl-ether-sulphate, the ether containing 2.2 mols of ethylene oxide | 12 g |
| Hydroxypropylmethylcellulose | 0.4 g |
| Polymer of Example 4 | 3 g |
| Triethanolamine q.s.p. | pH 8 |
| Water q.s.p. | 100 g |

This shampoo facilitates the combing-out of wetted hair and causes the head of hair to exhibit a good hold after drying.

Example III

An anionic shampoo is prepared by mixing the following:

| | |
|---|---|
| Sodium $C_{12}$–$C_{14}$—alkyl-ether-sulphate, the ether containing 2.2 mols of ethylene oxide | 12 g |
| Hydroxypropylmethylcellulose | 0.4 g |
| Polymer of Example 12 | 3 g |
| Triethanolamine q.s.p. | pH 8 |
| Water q.s.p. | 100 g |

This shampoo facilitates the combing-out of wetted hair and causes the head of hair to exhibit a good hold after drying.

Example IV

A non-ionic shampoo is prepared by mixing the following:

| | |
|---|---|
| Compound* | 10 g |
| Lauric acid diethanolamide | 3 g |
| Polymer of Example 4 | 5 g |
| Triethanolamine q.s.p. | pH 7 |
| Water q.s.p. | 100 g |

*This compound has the formula $C_{12}H_{25}$—O—$[C_2H_{30}(CH_2OH)]_n$ H, n having a statistical value of 4.

This shampoo facilitates the combing-out of wetted hair and causes the head of hair to exhibit a good hold after drying.

Example V

Wavesetting Lotion

The following composition is prepared:

| | |
|---|---|
| Polymer of Example 3 | 1.0 g |
| Vinyl acetate crotonic acid copolymer marketed under the name TV 242 by Messrs. Hoechst | 1.0 g |
| Trimethylacetylammonium bromide | 0.1 g |
| Ethanol q.s.p. | 50% |
| Perfume | |
| Dyestuff | |
| Water q.s.p. | 100 g |

Spontaneous pH: 7.4

After application and drying, this lotion imparts softness to sensitised hair.

Example VI

Wavesetting Lotion

The following composition is prepared:

| | |
|---|---|
| Polymer of Example 6 | 1.0 g |
| Vinyl acetate crotonic acid copolymer marketed under the name TV 242 by Messrs. Hoechst | 1.0 g |
| Trimethylacetylammonium bromide | 0.1 g |
| Ethanol q.s.p. | 10% |
| 2-Amino-2-methyl-propan-1-ol q.s.p. | pH 8 |
| Water q.s.p. | 100 g | pH: 8.

Example VII

Brushing Lotion

The following composition is prepared:

| | |
|---|---|
| Polymer of Example 3 | 0.3 g |
| Vinyl acetate crotonic acid copolymer marketed under the name TV 242 by Messrs. Hoechst | 0.2 g |
| Trimethylacetylammonium bromide | 0.2 g |
| Ethanol q.s.p. | 50% |
| Perfume | |
| Dyestuff | |
| Water q.s.p. | 100 g |

Spontaneous pH: 7.5.

Example VIII

Brushing Lotion

| | |
|---|---|
| Polymer of Example 6 | 0.3 g |
| Vinyl acetate crotonic acid copolymer marketed under the name TV 242 by Messrs. Hoechst | 0.2 g |
| Trimethylacetylammonium bromide | 0.2 g |
| Ethanol q.s.p. | 50% |
| 2-Amino-2-methyl-propan-1-ol q.s.p. | pH 8.7 |
| Water q.s.p. | 100 g | pH: 8.7.

Example IX

A shampoo was prepared by mixing the following:

| | |
|---|---|
| Sodium ($C_{12}$–$C_{14}$)—alkyl-ether-sulphate, the ether containing 2.2 mols of ethylene oxide | 10 g |
| Hydroxypropylmethylcellulose | 0.5 g |
| Polymer of Example 15 | 5 g |
| Triethanolamine q.s.p. | pH 8 |

-continued

| | |
|---|---|
| Water, q.s.p. | 100 g |

Example X

The following wavesetting lotion was prepared:

| | |
|---|---|
| Polymer of Example 15 | 1.5 g |
| Copolymer TV 242 (HOECHST) | 1.1 g |
| Trimethylacetylammonium bromide | 0.1 g |
| Ethanol q.s.p. | 20% |
| 2-Amino-2-methyl-propan-1-ol, q.s.p. | pH 8 |
| Water, q.s.p. | 100 g |

We claim:

1. A random polymer represented by the formula $$\left[ \begin{array}{c} R-N-(CH_2)_x-Z \\ | \\ CO \\ | \\ H+NH-C_2H_3-CO- \end{array} \right]_m$$

UNIT A $$\left[ \begin{array}{c} R'-N-R'' \\ | \\ CO \\ | \\ -NH-C_2H_3-CO- \end{array} \right]_p \quad \left[ \begin{array}{c} \ominus\oplus \\ OM \\ | \\ CO \\ | \\ -NH-C_2H_3-CO- \end{array} \right]_q -D$$

UNIT B   UNIT C wherein

Z represents a mercapto radical or a sulphonic acid radical, said radical being free or in the form of an alkali metal or an alkaline earth metal salt, x is an integer from 2 to 6, R represents hydrogen or lower alkyl, each R' independently represents hydrogen, lower hydroxyalkyl, alkyl having 1 to 18 carbon atoms or alkenyl having at most 18 carbon atoms, each R' independently represents hydrogen, lower hydroxyalkyl or lower alkyl, or R' and R'' together with the nitrogen atom to which they are attached form a 6-membered ring which can contain, apart from the said nitrogen atom, an oxygen or nitrogen atom, M represents hydrogen, alkali metal or half an atom of an alkaline earth metal, D represents $$-N-(CH_2)_x-Z, \quad -N-R''$$
$$\phantom{-N}| \phantom{(CH_2)_x-Z, \quad -N}| $$
$$\phantom{-N}R \phantom{(CH_2)_x-Z, \quad -N}R'$$

or $\ominus$—$OM^\oplus$ wherein R, x, Z, R', R'' and M have the meanings given above, m is a positive integer corresponding to the number of A units in the polymer, and p and q are each independently 0 or a positive integer corresponding to the number of B and C units, respectively, in the polymer, such that the sum m+p+q is from about 15 to about 500.

2. A polymer according to claim 1 in which the individual radicals R' and R'' are such that there are up to 10 different B units.

3. A polymer according to claim 2 in which the individual radicals R' and R'' are such that there are 1 to 3 different B units.

4. A polymer according to claim 1 in which Z is in the form of a sodium, potassium, magnesium, calcium, strontium or barium salt.

5. A polymer according to claim 1 in which R represents alkyl having 1 to 4 carbon atoms.

6. A polymer according to claim 1 in which R' or R'' represents hydroxyalkyl having 2 to 4 carbon atoms.

7. A polymer according to claim 1 in which R' and R'' together represent a pentamethylene, 3-oxa-pentamethylene or N-methyl-3-aza-pentamethylene group.

8. In a cosmetic composition suitable for application to human hair, said composition being in the form of a shampoo, a hair wave setting lotion, or a hair brushing lotion, wherein the improvement comprises improving the hold of the hair and imparting bulk and springiness thereto, said composition containing 0.1 to 10 percent by weight of at least one polymer as defined in claim 1.

* * * * *

UNITED STATES PATENT AND TRADEMARK OFFICE
CERTIFICATE OF CORRECTION

PATENT NO. : 4,363,797
DATED : December 14, 1982
INVENTOR(S) : Bernard JACQUET, et al It is certified that error appears in the above-identified patent and that said Letters Patent is hereby corrected as shown below:

IN THE HEADING:

At Section [63] entitled "Related U.S. Application Data", please correct the Serial No. to read:

--941,573--.

Signed and Sealed this

Twelfth Day of June 1984

[SEAL]

Attest:

GERALD J. MOSSINGHOFF

Attesting Officer     Commissioner of Patents and Trademarks